(12) United States Patent
Chien et al.

(10) Patent No.: US 11,083,388 B2
(45) Date of Patent: Aug. 10, 2021

(54) GIGAHERTZ FREQUENCY FRINGING NEAR-FIELD CARDIOVASCULAR SENSOR

(71) Applicants: Jun-Chau Chien, Berkeley, CA (US); Stanley Yuanshih Chen, Cupertino, CA (US)

(72) Inventors: Jun-Chau Chien, Berkeley, CA (US); Stanley Yuanshih Chen, Cupertino, CA (US)

(*) Notice: Subject to any disclaimer, the term of this patent is extended or adjusted under 35 U.S.C. 154(b) by 1299 days.

(21) Appl. No.: 15/344,571

(22) Filed: Nov. 6, 2016

(65) Prior Publication Data

US 2017/0135600 A1    May 18, 2017

Related U.S. Application Data

(60) Provisional application No. 62/255,529, filed on Nov. 16, 2015.

(51) Int. Cl.
*A61B 5/00*    (2006.01)
*A61B 5/0507*    (2021.01)
*A61B 5/024*    (2006.01)

(52) U.S. Cl.
CPC ........ *A61B 5/0507* (2013.01); *A61B 5/02405* (2013.01); *A61B 5/02438* (2013.01); *A61B 5/6801* (2013.01); *A61B 5/6887* (2013.01); *A61B 5/7207* (2013.01); *A61B 5/7225* (2013.01); *A61B 5/742* (2013.01); *A61B 5/6893* (2013.01); *A61B 5/6898* (2013.01); *A61B 2562/0228* (2013.01)

(58) Field of Classification Search
None
See application file for complete search history.

(56) References Cited

U.S. PATENT DOCUMENTS

| 10,660,531 | B1* | 5/2020 | Libove | A61B 5/0476 |
| 2010/0022900 | A1* | 1/2010 | Peterson | A61B 5/029 600/508 |
| 2010/0027737 | A1 | 2/2010 | Mostov | |
| 2015/0018676 | A1 | 1/2015 | Barak | |
| 2016/0228010 | A1 | 8/2016 | Kim | |

* cited by examiner

*Primary Examiner* — Joel F Brutus
(74) *Attorney, Agent, or Firm* — Stephen E. Zweig

(57) ABSTRACT

A near-field sensor method and device for obtaining cardiovascular information is disclosed. A transmission-line aperture arrangement configured to guide electromagnetic waves and emit near-field fringing energy, is placed near the skin. The transmission line is excited at a narrow-band Gigahertz frequency. The near-field fringing energy emitted by the sensor device penetrates at least partially into the skin and underlying blood vessels, and this energy is partially absorbed and partially phase shifted in a time varying manner according to the changes in physiology of the skin. The status of the sensor device is monitored over a plurality of time intervals, and changes in both the phase and the amplitude of the signals passing though the transmission line are used to determine the cardiovascular information such as heart rates. Various transmission-line configurations, and various reference transmission-line methods to reduce low-frequency noise, are also discussed.

21 Claims, 15 Drawing Sheets

A - A'

GIGAHERTZ FREQUENCY FRINGING NEAR-FIELD CARDIOVASCULAR SENSOR

CROSS REFERENCE TO RELATED APPLICATIONS

This application claims the priority benefit of U.S. provisional application 62/255,529, "MICROWAVE NEAR-FIELD HEART-RATE SENSOR", filed Nov. 16, 2015; the entire contents of which are incorporated herein by reference.

BACKGROUND OF THE INVENTION

Field of the Invention

The present invention relates to the field of cardiovascular and heart rate detecting sensors. More specifically, the invention relates to miniaturized cardiovascular sensors that are easily integrated as a part of wearable devices, such as wristbands, watches, finger clips, rings, and chest straps, using fringing near-field Gigahertz frequency sensors.

Description of the Related Art

Conventional cardiovascular and heart-rate sensors can be categorized into various different types:

A first type of heart-rate sensor is based on optical photoplethysmogram (PPG) methods, which have been widely adopted in the pulse oximetry field. In this optical method, one or more light emitting diodes (LEDs) are used to shine light onto (and into) the skin. One or more photodetectors are used to measure the amount of attenuation or reflection of this light, which is dependent on the light absorption characteristics of the tissue, as well as the status of the blood flowing through the blood vessels underneath the skin. Using this method, various cardiovascular signals, such as blood oxygen levels and heart rate, can be extracted by measuring changes in these photodetector signals.

Such optical approaches are widely adopted in many commercial wearable devices including the Apple Watch and Samsung Gear Fit. However, there are various disadvantages to an optical-based detection scheme. One is that the optical signal is sensitive to the skin color and the amount of sweat. Another is that such methods often require high power consumption to drive the LEDs. Another disadvantage is that such optical methods often require a relatively complicated industrial design to accommodate the required LEDs and photodiodes, which can increase cost and limit design flexibility.

Another type of heart-rate sensor uses skin contacting electrodes to measure changes in electrical properties, such as changes in the skin and tissue electrical impedance. These measurements are often done using either DC (direct current) or a low frequency (e.g. under a few kilohertz) stimulus.

Typically an injection current is supplied to the subject (patient or user) using electrodes that are in direct contact with the skin. The tissue impedance, which changes according to the blood flow caused by the cardiovascular status of the patient (e.g. heart beat), is detected by using another pair of electrodes to measure the voltage changes along the current path at two or more specific spots. Such impedance-based approaches are presently used in the popular Jawbone UP3 and UP4 fitness trackers for heart-rate measurements.

However, there are also some disadvantages to impedance based detection schemes as well. One disadvantage is that the detection requires several electrodes in direct contact with the skin. This not only complicates the industrial design of the packaging (resulting in increased cost) and also limits the appearance of the wearable devices. Another disadvantage is that the measuring electrodes must be separated far enough away from each other in order to increase the chances of detecting changes in the tissue impedance. This poses a considerable constraint for wearable devices, since many otherwise desirable designs may not have enough space to accommodate all of the electrodes. For example, the Jawbone UP3 and UP4 require that the electrodes be distributed along a wristband. Another potential drawback is skin irritation caused by electrode contact. Further, such direct skin-electrode contact methods generate signals that can be easily distorted by irrelevant changes in the user's skin condition, such as sweat which can distort tissue impedance measurements. Finally, in order to achieve a good signal to noise ratio (SNR), such methods also consume a fair amount of electrical power at hundreds of microampere. The requirement of current injection complicates the electronic design in order to meet the safety standards.

Another type of electrode based cardiovascular status sensors are based on measuring electrocardiogram (ECG) signals from the chest, or other locations of the body such as the fingertips or hands. These methods also require that device electrodes be placed in direct contact with the user's skin in order to form a closed loop to determine changes in the user's body electrical status. Therefore this ECG approach tends to suffer from disadvantages that are similar to the bio-impedance measurements problems discussed previously. The electrical power of the ECG sensor is less than that of the bio-impedance measurements since a stimulus is not necessary.

Another type of cardiovascular status measurement sensor uses far-field Doppler radar techniques by transmitting and receiving electromagnetic (EM) waves through the use of several antennas. In one approach, a frequency-modulated continuous-wave (FMCW) radar module is used to transmit far-field radiofrequency signals that rapidly sweep through a broad range of frequencies over durations of tens of microseconds. The distance and the motion of the targeting objects are measured through the Doppler shift presented in the received propagating waves. In another approach, a pulse train is transmitted, and the target is detected by measuring the time-of-flight (ToF) from the receiving echoes. The pulses are typically short in duration, with a pulse-width time on the order of nanoseconds, meaning that the system needs to accommodate ultra-wideband frequencies, e.g. 3.1-10.6 GHz.

These methods appear to be better suited to detecting changes in larger blood vessels such as arteries, rather than smaller blood vessels such as capillaries. As the patient's arteries expand or contract during each pulse cycle, the motion of the expanding or contracting artery causes a Doppler shift in the reflected far-field radio signals. These Doppler shifts can be analyzed for frequency changes using Fourier analysis and other methods. Thus as the user's artery underneath the user's skin changes shape as blood flow changes during a heartbeat, and these Doppler radar methods detect these changes in the received signals as changes in motion induced time-of flight (TOF) and Doppler shifts.

This Doppler radar type of method is exemplified by the work of Mostov (US 2010/0027737), Barak (US 2015/0018676) and Kim et. al. (US 2016/0228010).

To operate, devices based on these Doppler radar methods are typically positioned close to certain locations on the user, such as the wrist, where the underlying arteries are optimally positioned. Although these methods require no direct contact with the subject's skin these methods also suffer from various disadvantages. In particular, since the arteries are not uniformly distributed throughout the body, Doppler radar based sensors may not work with equal efficiency throughout the body. In particular, they may require more precise positioning over arteries that exhibit sufficient movement in order for the Doppler radar methods to work. This can be a potentially significant drawback. In addition, the Doppler radar system needs at least two antennas, one transmitting and one receiving, which can consume large amount of device area, and thus severely limits the form factor. Another drawback is that the radiation patterns of the antenna are altered considerably due to the loading of the human tissue when the Doppler radar system is close to the human skin. The inhomogeneity of the human tissue deteriorates the power matching condition and degrades the signal-to-noise ratio (SNR). Usually high electrical power consumption is necessary in these Doppler radar systems to recover the losses in the signal-to-noise ratio.

BRIEF SUMMARY OF THE INVENTION

The invention is based, in part, on the observation that prior art electronic heart-rate monitoring devices and methods are not entirely satisfactory. In particular, prior art Doppler radar based methods suffer from various deficiencies:
  High transmitting power is often necessary as electromagnetic waves experience attenuation when propagating in the air or dielectrics.
  Prior art RF based devices often require at least two antennas, one transmitting and one receiving, for proper operation. These antennas tend to occupy a significant amount of area and can limit the form factor of the monitoring device.
  Antenna RF radiation patterns can change significantly in the proximity of human skin due to the loading of the tissue. This can affect both antenna matching and the RF radiation efficiency. Such effects are often difficult to compensate for, as human tissues can exhibit large variations both between persons and even within different sites for a single person.
  Doppler radar based methods may require close proximity to arteries to operate, and thus may be more position sensitive and less flexible than optimal.
  The rejection of motion artifacts can require sophisticated signal processing approaches to extract heartbeat-related motions from background signals.

The invention is based, in part, on the insight that it would be useful to provide heart-rate or other cardiovascular status measurements that offer low power consumption to facilitate continuous monitoring, in particular with small, battery operated, equipment.

The invention is also based, in part, on the insight that it would be useful provide electromagnetic type heart-rate or other cardiovascular status measurements that require no conductive electrodes, usually a metallic material, in contact with the user's skin such as bio-impedance and ECG measurements.

The invention is also based, in part, on the insight that it would be useful to provide heart-rate or other cardiovascular status measurements that are insensitive to the user's skin color.

The invention is also based, in part, on the insight that it would be useful to provide heart-rate or other cardiovascular status methods using techniques that simplify monitoring device industrial design. In particular, methods that facilitate use of wearable cardiovascular sensors that lack drill holes or protruding electrodes to irritate the patient's skin or collect sweat would be useful.

The invention is also based, in part, on the insight that it would be useful to provide heart-rate or other cardiovascular status measurements that offer small form size, where the form size need not substantially vary as function of the frequency of the electrical and RF signals used in the measurement process.

The invention is also based, in part, on the insight that use of fringing near-field methods, in particular fringing near-field methods that employ near-field Gigahertz changing electrical fields and magnetic fields, may be useful towards achieving the above objectives.

Thus, as will be discussed, the invention is based, in part, on the insight that a method and apparatus that employs a near-field fringing electromagnetic sensor that couples these near-fields to the skin, and detects the changes in the flow of blood through the user's blood vessels (e.g. capillaries, arteries, veins) may particularly useful towards achieving at least some of the above objectives.

In some embodiments of the invention, an electronic transmitter device typically drives a transmission-line type electromagnetic sensor, usually positioned near the skin of a user, at Gigahertz frequencies (usually 0.5 to 60 GHz). To allow for lower energy consumption, this transmitter may operate on a schedule or duty cycle that only sends a narrow band (e.g. 0-10 MHz wide) burst of excitation at Gigahertz frequency (often called a signal) for short periods of time, such as 1 to 5 microseconds. However if lower energy consumption is not as important an objective, then broader band bursts of excitation (signals) for longer periods of time, such as 10 microseconds or longer, may also be used. In other embodiments, excitation bursts at multiple frequencies may also be used.

This near-field excitation burst is perturbed by the physiology of the skin. This can change the phase or amplitude of the excitation burst as it travels through the transmission line, and an electronic receiver can detect this perturbed signal by measuring its changes in any of the phase, amplitude of the signal.

This scheme has certain advantages over alternative approaches, because near-field coupling between this excitation burst (signal) and the physiological structure of the skin and underlying tissues (such as blood vessels) can be relatively efficient. As a result, this type of near-field detection mechanism enables the use of a low-power excitation sources, thus providing increased power efficiencies over prior art. The near-field fringing methods also have the additional advantage over prior art electrode based methods, in that cardiovascular status (e.g. heart rate) can be detected without direct electrode contact with the user's skin.

As will be discussed, in some embodiments, the invention may be a near-field sensor method and/or device for obtaining user cardiovascular information. This system often operates by disposing one or more transmission lines configured to guide short bursts of narrow band (typically 0.01 GHz wide), Gigahertz frequency (typically 0.5 to 60 GHz) electromagnetic waves (excitation bursts) and to emit near-field fringing energy proximate the skin of the user. Here "proximate" typically means within about 1-2 millimeters or less, but need not mean direct contract with the skin. Often a thin membrane of a plastic or glass material may be disposed between the transmission line and the skin so that there is no actual contact with the skin.

The system will typically be configured so that near-field fringing energy emitted by this transmission line, when operating at Gigahertz frequencies, extends far enough away from the transmission line so as to penetrate at least partially into blood vessels of the user's skin. The system will then excite this transmission-line with the narrow-band Gigahertz frequency signal over a plurality of time intervals (often 1 to 5 microseconds) often at a rate of 10-100 Hz. The system obtains data by measuring changes in any of the phase or amplitude of the near-field fringing energy over this plurality of time intervals. This data can then be analyzed, typically using a processor (e.g. microprocessor, microcontroller, computer processor) and used to determine various cardiovascular parameters, such as the heart rate (pulse) of the user.

DETAILED DESCRIPTION OF THE INVENTION

Figure 1:
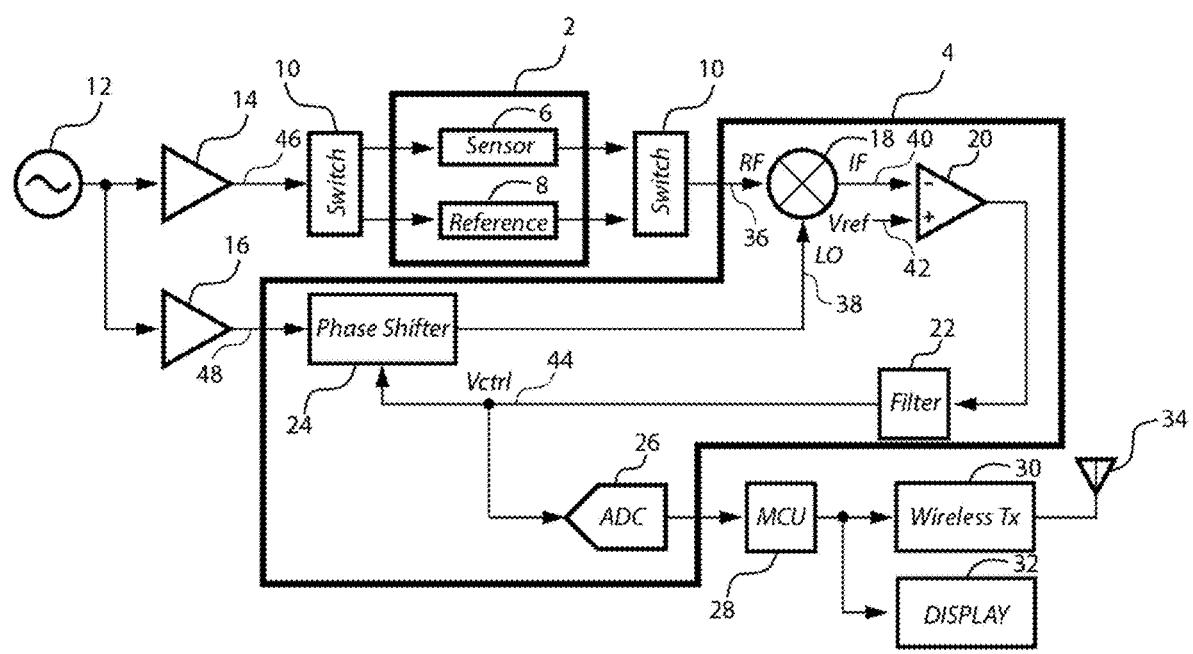
FIG. 1 is a system block diagram of the invention.

Gigahertz radio, microwave, and millimeter-wave frequency signals are often handled using microstrip structures. Such structures can include thin conducting traces on the circuit boards, and the like, and have the advantages of being both physically small, easy to configure, and inexpensive to manufacture. One aspect of such structures, which is useful for some of the embodiments described herein, is that the near-field electric fields from these structures penetrate for short distances from the edge of one of the conducting traces into the air regions and the nearby materials around the structure.

The depth of the penetration is often controlled by the gap or aperture size between the conducting traces. For example, the penetration depth is roughly equal to the substrate thickness in a microstrip transmission line. In another example, the penetration depth is roughly the gap between the centered signal line and the two adjacent ground traces in a coplanar waveguide (CPW). These fringing electric fields are in turn affected by the physical properties, such as the complex permittivity, of the nearby structures, and this can influence the phase and the amplitude of the electromagnetic waves that generates these fringing fields.

Physiological considerations: As a rough approximation, the epidermis (the outer layer of skin) is a waterproof structure with many dead skin cells (the stratum corneum), as well as other cells, and this epidermis is often less affected by the cardiovascular status of the user (e.g. does not change its structure or electrical properties as much depending upon the user's heartbeat). Underneath the epidermis is the dermis, which often contains smaller blood vessels (often capillaries) that do change their structures and electrical properties according to the patient's cardiovascular status. In particular, those capillaries carrying oxygenated blood will tend to react to pressure and oxygenated blood from the patient's arteries, and this can impact how this capillary interacts with near-field electrical and magnetic fields.

The arteries and veins are larger structures; often located still further away from the epidermis, below the dermis, lower levels, such as in the subcutis (hypodemis). These larger blood vessels are not uniformly distributed however, but rather are concentrated in certain regions of the body. The arteries undergo significant changes in structure with every pulse, and are often a frequent target for blood pulse and other cardiovascular status target measurements as a result. However methods that can operate with the smaller and more uniformly distributed capillary type blood vessels are advantageous because the sensors do not need to be located so precisely. By contrast, some prior art methods (such as the previously discussed Doppler radar methods)

that operate by detecting changes in artery properties need to be located relatively precisely over a given artery.

Thus as previously discussed, in some embodiments, the invention may be a near-field sensor method of obtaining user cardiovascular information. This user may be a human user, such as an ambulatory human using the device for sports or routine fitness purposes, or for medical use, such as to obtain the cardiovascular status of a patient. However the device may also be used for animal or veterinary purposes as well, and in this case, the user may be an animal.

As previously discussed, in this embodiment at least one transmission line configured to guide electromagnetic waves and to emit near-field fringing energy will be provided and disposed (e.g. positioned) proximate a skin of a user. In this embodiment, the configuration of the transmission line (and any aperture or gap) and the proximity to the user will be such that near-field fringing energy emitted by this at least one transmission-line, when operating at Gigahertz frequencies, extends far enough away from the transmission line so as penetrate at least partially past the outer layer of the skin (at least past the stratum corneum layer) and into the blood vessels of the skin.

In this context, "into the blood vessels of the skin" means at least into the capillaries of the skin. Further, in some embodiments, this may also mean penetrating into the underlying arteries and veins of the user that are disposed deeper in the skin, or even below the skin.

This at least one transmission-line will be excited with narrow-band Gigahertz frequency signal over a plurality of time intervals (often 1 to 5 microseconds), often at a rate of 10-100 Hz. Near field fringing energy from this at least one transmission line will couple with the various structures (e.g. blood vessels) in the skin and beneath the skin, and these physiological effects will somewhat distort the signals as they flow through the at least one transmission line. In particular, the physiological effects may cause changes in the phase and/or amplitude of the original signals (excitation signal pulses/bursts). The signals emerging from the transmission line (often at the other end of the line) can be measured, and changes in any of the phase or amplitude of this near-field fringing energy over the plurality of time intervals determined, often with the aid of at least processor (e.g. microcontroller, microprocessor or other computer type processor). This at least one processor, and the data, can be used to determine cardiovascular data of interest, such as at least the heart rate of the user.

Among other distinctions from prior art, note that in addition to employing near-field rather than far field techniques, the methods discussed herein generally rely on narrow-band Gigahertz frequencies. That is, the actual signal transmitted throughout an entire series of measurements may often be at the same fixed frequency, and this fixed frequency may have a bandwidth of 0.01 GHz (e.g. 10 MHz) or less.

So according to the invention, one device might operate by sending a series of pulsed carrier signal at 10 GHz with each pulse lasting for 1 microsecond at a pulse repetition rate of 100 Hz. Another device might operate by sending a series of pulsed carrier signal at 5 GHz with each pulse lasting for 10 microseconds at a pulse repetition rate of 10 Hz.

This fixed frequency may be any value between 0.5 to 60 GHz. The bandwidth of the signals sent at the fixed frequency may be between 0 to 10 MHz wide. This is why the technique is described as "narrow-band Gigahertz frequencies", while at the same time, the device is described at operating at a given frequency between 0.5 to 60 GHz.

By contrast, among other differences, prior art Doppler radar based methods, such as US patent publication 2015/0018676, operate by, during a single measurement (signal burst), sweeping a range of frequencies, such as 3.1 to 10.6 GHz, during a burst sweep time of 10 microseconds. Under prior art, over the 10 microsecond pulse width (burst width) of the 2015/0018676 individual determination, a wide range of frequencies between 3.1 to 10.6 GHz would be used.

However in other embodiments, it may be useful to emit these narrow-band Gigahertz frequency signal pulses or bursts at more than one frequency, such as at two or three narrow band frequencies simultaneously. In these embodiments, these narrow-band Gigahertz frequency signal pulses or bursts, which are emitted over a plurality of time intervals, can be emitted at a plurality of discrete, narrow bandwidth, frequencies.

To further distinguish over prior art, note that, as previously discussed, the present techniques use the near-field fringing effect from a non-radiating microstrip structure. This near-field fringing energy penetrates on an order of a width of a gap or aperture between the at least one transmission line and a nearby ground plane. Note that the net effect of this gap constraint is to limit the maximum extent that the near fields can penetrate into, meaning that the penetration depth is strongly geometrically dependent and not frequency dependent.

The invention can be viewed as being a transmission line that carries a guided electromagnetic wave, which is sensitive to its nearby environment. As the electromagnetic waves traverse along this guided transmission line, in essence the speed of the wave and the energy lost (into heat) are affected by the objects that come in close proximity to the transmission line.

According to the invention, the blood vessels, which have dimensions and blood flow that change with time according to the cardiac status of the user, are the objects that come into close proximity to the transmission line. Note that because we are operating in the near-field region, however, these effects operate by changing electrical fields and changing magnetic fields, rather than by classical electromagnetic radiation, which is a far-field effect.

The invention guides the propagating electromagnetic waves using transmission lines, and therefore the fringing fields are confined locally in proximity to the transmission lines. Thus in contrast to prior-art methods that use radar methods and electromagnetic radiation (far field effects), the invention produces a non-radiating sensor.

However part of the fringing fields, instead of terminating at the other conducting traces, can leak away and convert into propagating waves. In transmission line sensor such as microstrip or stripline architecture, the amount of leakage is small, usually less than 1% of the near-field emitting energy. Such radiation effect can potentially be used for detecting cardiovascular information; however, it usually results in much lower signal-to-noise ratio due to its low emitting energy. In this context, the at least one transmission line used in the invention can also function as an antenna and emit far-field microwave frequency electromagnetic radiation at distances greater than the wavelength, $\lambda$. The invention will primarily operate by using at least one of:

A: The reactive near-field, wherein the near-field fringing energy emitted by the at least one transmission-line, when excited at Gigahertz frequencies extends up to $\lambda/2\pi$ times a wavelength of the Gigahertz frequency away from the at least one transmission-line.

B: The Fresnel near-field, wherein the near-field fringing energy emitted by the at least one transmission-line extends up to the wavelength λ.

In the following discussions, some specific examples and embodiments of the invention are given, and some actual data produced by the invention is also presented. Before commencing with these more detailed discussions, some acronym definitions will be useful.

Acronym definitions: Throughout this specification, various common electrical engineering and circuit design acronyms are used. Some of these acronyms are defined in Table 1 below as follows:

TABLE 1

Definition of certain acronyms

| Acronym | Definition/Description |
|---|---|
| PCB | Printed circuit board |
| PPG | Photoplethysmogram |
| LED | Light emitting diode |
| DC | Direct current |
| SNR | Signal-to-noise ratio |
| ECG | Electrocardiogram |
| FMCW | Frequency-modulated continuous wave |
| RADAR | Radio detection and ranging |
| TOF | Time-of-flight |
| I/Q | In-phase/quadrature-phase |
| CW | Continuous wave |
| TDM | Time-division multiplexing |
| CDS | Correlated double sampling |
| ADC | Analog-to-digital converter |
| LO | Local oscillator |
| RF | Radio frequency |
| MCU | Micro-controller unit |
| PC | Personal computer |
| HRV | Heart-rate variability |
| Tx | Transmitter |
| Rx | Receiver |
| TRx | Transceiver |
| Vref | Reference voltage |
| DTC | digital-to-time converter |
| VCO | Voltage-controlled oscillator |
| DLL | Delay-locked loop |
| PLL | Phase-locked loop |
| TDC | Time-to-digital converter |
| FET | Field-effect transistor |
| LNA | Low-noise amplifier |
| CMOS | Complementary metal-oxide-semiconductor |
| SiGe | Silicon germanium |
| SAR | Successive approximation register |
| MEMS | Microelectromechanical system |
| Q | Quality factor |
| CPW | Coplanar waveguide |
| GCPW | Grounded coplanar waveguide |
| SRR | Split-ring-resonator |
| CSRR | Complementary split-ring-resonator |
| EM | Electromagnetic or electromagnetics |
| SPDT | Single-pole double-throw |
| BPM | Beats per minute |

Note that in the example shown in FIG. 1; more than one transmission line is used. That is, the at least one transmission line previously discussed comprises at least one sensing transmission line 6, and at least one reference transmission line 8. Use of such reference transmission-line methods can help further reduce noise and other extraneous signals.

In FIG. 1 and a number of the subsequent figures, the invention is further exciting at least one sensing transmission line 6, and at least one reference transmission line 8, according to various methods, including time-division multiplexing and chopping stabilization methods. These methods generally alternate the signal pulses between the at least one sensing transmission line 6, and at least one reference transmission line 8. (In these figures, only one sensing transmission line and only one reference transmission line are shown).

As will be discussed, the invention measures changes in any of the phase or amplitude of the near-field fringing energy from the one sensing transmission line 6 and the reference transmission line 8 over a plurality of time intervals (this is needed to detect changes in physiology over time, such as the changes caused by the patient's heartbeat). The invention uses changes in any of the phase or amplitude of the near-field fringing energy obtained from the reference transmission line 8 to correct data (e.g. from the sensing transmission line) for noise or drift.

The structural differences between the sensing transmission line configuration 6 and the reference transmission line configuration 8 will be discussed in more detail in FIGS. 3A and 3B as well as subsequent figures. However briefly, often the reference transmission line 8 is configured to shield or block any near field energy from that may have penetrated at least partially into the blood vessels of the skin. So in essence, the reference transmission line 8 operates as the "control" for the "experiment" physiological signal detected by the sensing transmission line 6.

FIG. 1 shows a block diagram of one embodiment of the invention. An excitation source 12 generates a continuous-wave (CW) signal at microwave frequencies. The excitation signal is split into two using a pair of driving amplifiers 14 and 16. One of the driving amplifiers 14 drives a pair of nearly identical near-field sensor/reference units 2. In such a pairing configuration, one reference line 8 serves as the reference whereas the other sensor line 6 serves to detect, for example, the modulation of the blood volume in the user's blood vessels due to heartbeats.

The two sensor/reference units 2 can be operated in time-division multiplexing (TDM) scheme using single-pole double-throw (SPDT) switches 10. The controls of the two switches 10 can operate coherently at a chopping rate. In this example, the switches 10 direct the excitation signal either to the sensing transmission line 6 or the reference transmission line 8 in a ping-pong fashion, which enables the application of correlated double sampling (CDS) applied after ADC samples or continuous-time chopping stabilization on the measured signal to mitigate the drift induced by the environmental parameters such as the temperature and the flicker noise induced by the rapid chopping circuits.

The changes in the blood volume modulate both the amplitude and the phase of the signal propagating in the sensing transmission line 6 through field coupling. In this example, the time-varying amplitudes and phases are detected using a phase-sensitive detector block 4 (shown in FIG. 1) comprising a mixer 18 with its RF port driven by the sensing signal 36 from the sensor 6, and the LO port driven by the signal coming from the driving amplifier 16.

The mixer 18 can be configured using a phase shifter 24 to detect the amplitude change by adjusting the phase of the LO signal 38 to be in-phase with respect to the RF signal 36. Alternatively, the mixer 18 can be configured to detect the phase change by adjusting the phase of the LO signal 38 to be in quadrature phase with respect to the RF signal 36. Since both the RF and the LO signals are at the same frequency, the amplitude and the phase information are down-converted to near-DC frequencies at the output of the mixer 18. As shown in FIG. 1, a baseband amplifier 20 boosts the signal and a filter 22 rejects the out-of-band interference and the second-order harmonics. An analog-to-digital converter (ADC) 26 digitizes the signal and a micro-controller unit (MCU) 28 performs additional signal processing including but not limited to (1) the extraction of instantaneous heart rate and (2) the analysis of the heart-rate variability (HRV). The measured heart-rate information is shown on a display 32 included in the device. Furthermore, the heart-rate information can be wirelessly transmitted using a wireless transmitter (Tx) 30 to a mobile phone or a console such as a personal computer (PC).

Thus in some embodiments, the invention may further use changes in any of the phase or amplitude of the near-field fringing energy obtained from the at least one reference transmission-line 8, and automatic feedback adjustment, to correct for various sources of noise or drift. These undesired effects can include skin-sensor contact variations, and/or changes caused by noise or drift in any of the phase or amplitude of the near-field energy signal obtained from the at least one sensing transmission line 6.

As discussed here, various methods may be used to, according to various combinations, to detect changes in the phase of the near-field fringing energy from the sensing transmission line(s) 6.

One method is to detect the physiologically modulated RF carrier signal from the sensing transmission line 6, and use a mixer and a phase adjustable local oscillator (LO) to detect physiologically induced changes in the phase of the physiologically modulated RF carrier signals.

Alternatively or additionally, the invention may operate by adjusting the phase of an RF signal that excites the sensing transmission line 6 and the reference transmission line 8, using multiplexing and/or chopping methods to switch back and forth between the sensing transmission line 6 and the reference transmission lines 8. The invention (often using the processor) can compare phase changes between the detected physiologically modulated RF carrier signals from the sensing transmission line 6, and the detected non-physiologically modulated RF carrier signals from the reference transmission line 8.

Note that the chopping or multiplexing methods used herein can often cause some undesired electronic noise (flicker noise). This noise can be further removed by various methods such as by employing double-edges correlated-double sampling (CDS) methods.

Note that although, as previously discussed, the invention can operate with narrow-band excitation frequencies (e.g. exciting the transmission lines with narrow-band Gigahertz signals), the device can be driven at wide range of different frequencies as desired. That is, it is the transmission line, and not the sensing device acting as a resonator, that operates only at a given designated frequency. So the basic device is capable of being driven at a wide range of frequencies, such as the 0.5 to 60 GHz, range even though the actual transmission line will often be driven at a specific narrow-band frequency determined by the electronic design choices. Based on experimental work, it has been found that frequencies of from about 1-26 GHz produce good heart-rate signals, such as the signals that will be discussed in FIG. 3E.

More specifically, in some embodiments, the down-converted signal 40 can be used as a feedback control signal to adjust the phase of the phase shifter 24. The feedback operation automatically adjusts the phase shift of the LO signal 38 to enable the locking of the mixer output 40 to a reference voltage 42 (Vref), also shown in FIG. 1. For example, when setting Vref to 0 V, the feedback will null the mixer output 40 by adjusting the phase of the LO signal 38 using the phase shifter 24 such that the RF 36 and LO 38 signals input to the mixers are in quadrature. The main advantage of such an automatic feedback adjustment is the simplification of the calibration when the sensor 6 is in contact with the human skin.

Figure 2A:
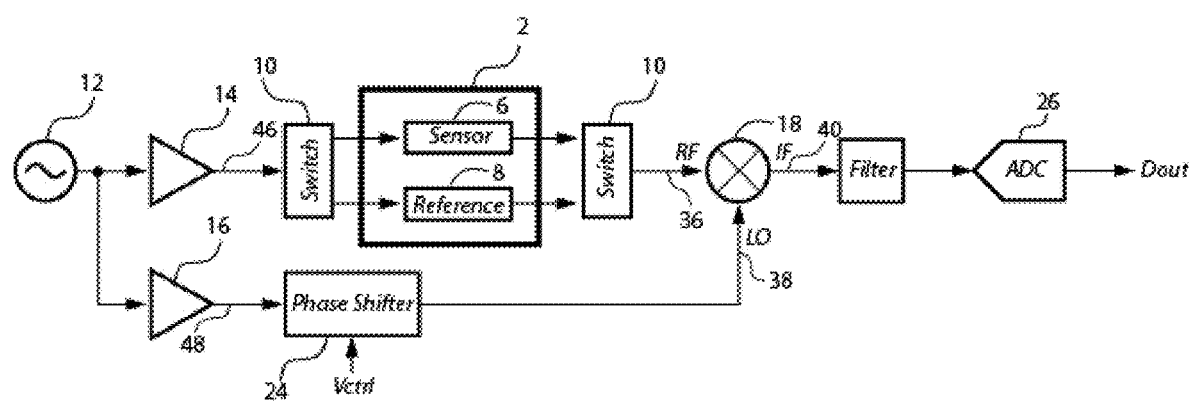
FIG. 2A is a system block diagram with open-loop measurements.
Figure 2B:
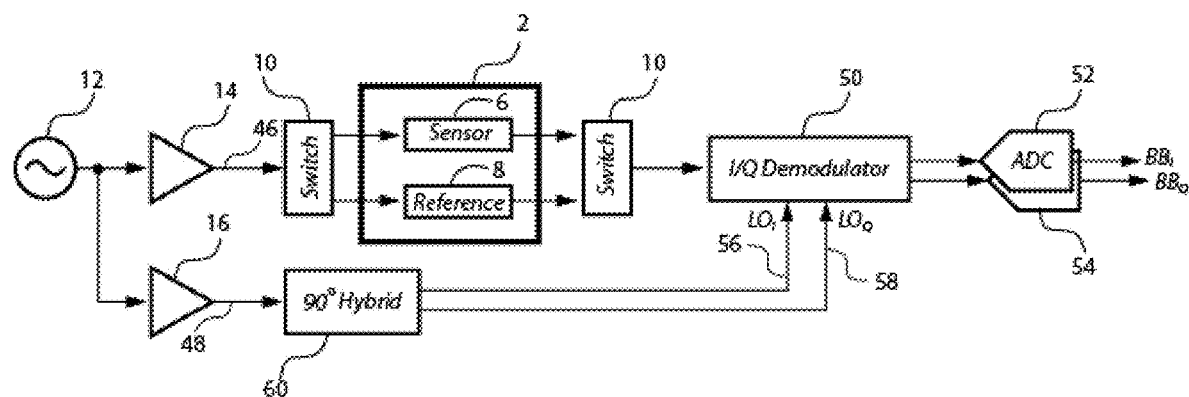
FIG. 2B is a system block diagram with open-loop measurements using I/Q mixers.

Compared to an open-loop operation, as shown in FIG. 2A and FIG. 2B, the closed-loop feedback operation not only saves power but also increases the detection speed. FIG. 2A is an open-loop architecture where an ADC 26 directly digitizes the down-converted signal 40. In such architecture, the initial phase calibration upon skin-sensor contact is accomplished in the foreground through an RF phase shifter or a digital-to-time converter (DTC). FIG. 2B is a variance of an open-loop architecture shown in FIG. 2A that omits the phase shifter 24 in FIG. 2A and uses a pair of I/Q mixers or demodulators 50 to extract both the amplitude and the phase information simultaneously. The amplitude change and the phase shift due to blood volume modulation are computed through arithmetic operation such as arctangent at digital backend. The I/Q LO signals 56 and 58 can be generated from a 90° hybrid 60.

In some embodiments whereas a feedback is employed (FIG. 1), it is important to note that the phase changes in the signal on the sensor 6, caused by the modulation of the blood volume in the blood vessels from the heartbeats, is reflected on the feedback control signal 44 (Vctrl). Therefore, as shown in FIG. 1, heart-rate information can be acquired by digitizing the feedback control signal 44 (Vctrl) using an ADC 26. Note that the illustrated feedback loop 4 is implemented using analog circuits and an ADC for digitization. The actual implementation can utilize an all-digital approach with a time-to-digital converter (TDC). In addition, the feedback loop 4 is similar to a delay-locked loop (DLL) where the mixer 18 serves the role of a phase detector. Therefore, a stable closed-loop operation can be readily achieved.

Figure 2C:
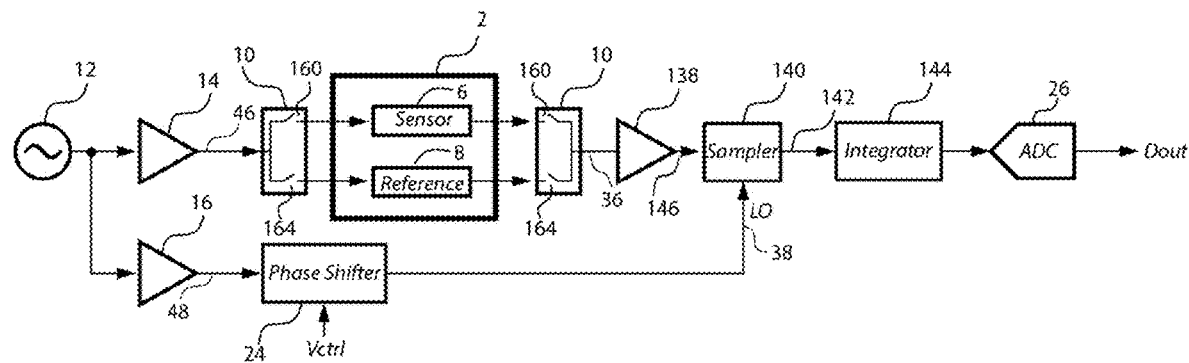
FIG. 2C is a system block diagram with open-loop measurements using sampler and integrators.
Figure 2D:
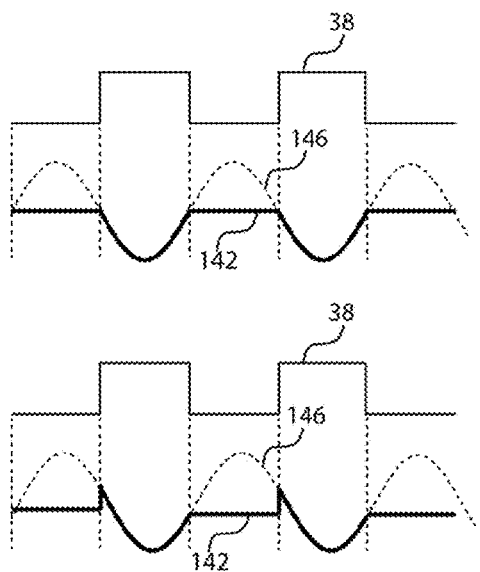
FIG. 2D is an illustration of the operation of the sampler as a phase detector.
Figure 2E:
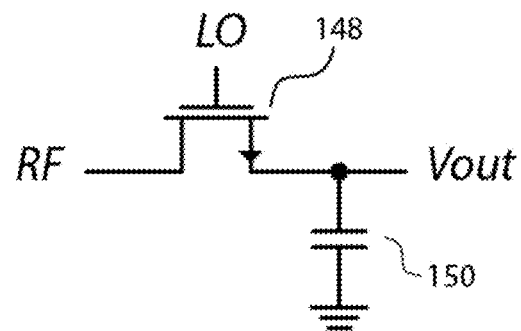
FIG. 2E is a schematic of a sampler.

In some embodiments, a phase-sensitive detection block can be implemented with a sampler 140. In FIG. 2C, the received signal is first amplified by the low-noise amplifier (LNA) 138 to the maximum voltage swing dictated by the supply voltage in order to minimize amplitude perturbation. As shown in FIG. 2D, the timing position of the signal transition edge is detected at sampler output 142 through a sampling switches implemented with field-effect-transistor (FET) 148 in SiGe, CMOS, or other semiconductor technologies (FIG. 2E). In particular, such a sampler is implemented as a sample-and-hold circuit with an on-chip capacitor 150. To reduce the sampling noise, integration is performed using a low-pass filter or an integrator 144. Such an integrator can be implemented using a low-power gm-C integrator.

Figure 2F:
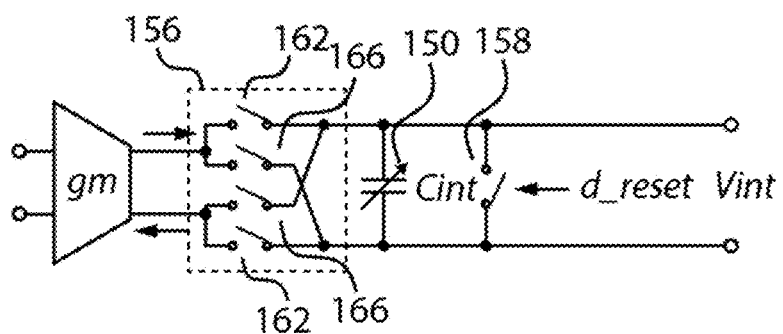
FIG. 2F is a schematic of the integrator with chopper stabilization technique.

In some embodiments, the RF carrier signal is alternated between the sensing and the reference elements at a chopping frequency ($f_{chop}$). Therefore the heart-rate signal is modulated to the chopping frequency away from the DC where the flicker noise is presented. To demodulate the chopping signal, a set of chopper switches 156 are implemented in the integrator (FIG. 2F). The idea is to periodically reverse the direction of the integration current at the chopping rate. In this way, the low-frequency flicker noise is automatically nulled after one complete chopping cycle. The operation sequence is described as follows (please refer to both FIG. 2C and FIG. 2F): (1) first, the integrating capacitor is reset through a bridge switch 158 (FIG. 2F); (2) after reset, the RF carrier signal is routed to the reference transmission line through RF switches 160 (FIG. 2C) and the noise is integrated through the chopping switches 162 (FIG. 2F) on to the integration capacitor 150 (FIG. 2F); (3) next, the RF carrier signal is directed to the sensing transmission line through the RF switches 164 (FIG. 2C), the chopping switches 162 are disabled, the chopping switches 166 are enabled, and both the heart-rate signal and the noise are integrated on to the capacitor 150; (4) last, the signal is hold and the following ADC digitizes the signal. In some embodiments, both the integration capacitance and the integration duration are adjustable to control the integrator gain. Note that the integration capacitor 150 can be implemented using the input capacitance of an on-chip successive approximation analog-to-digital converter (SAR-ADC).

Figure 2G:
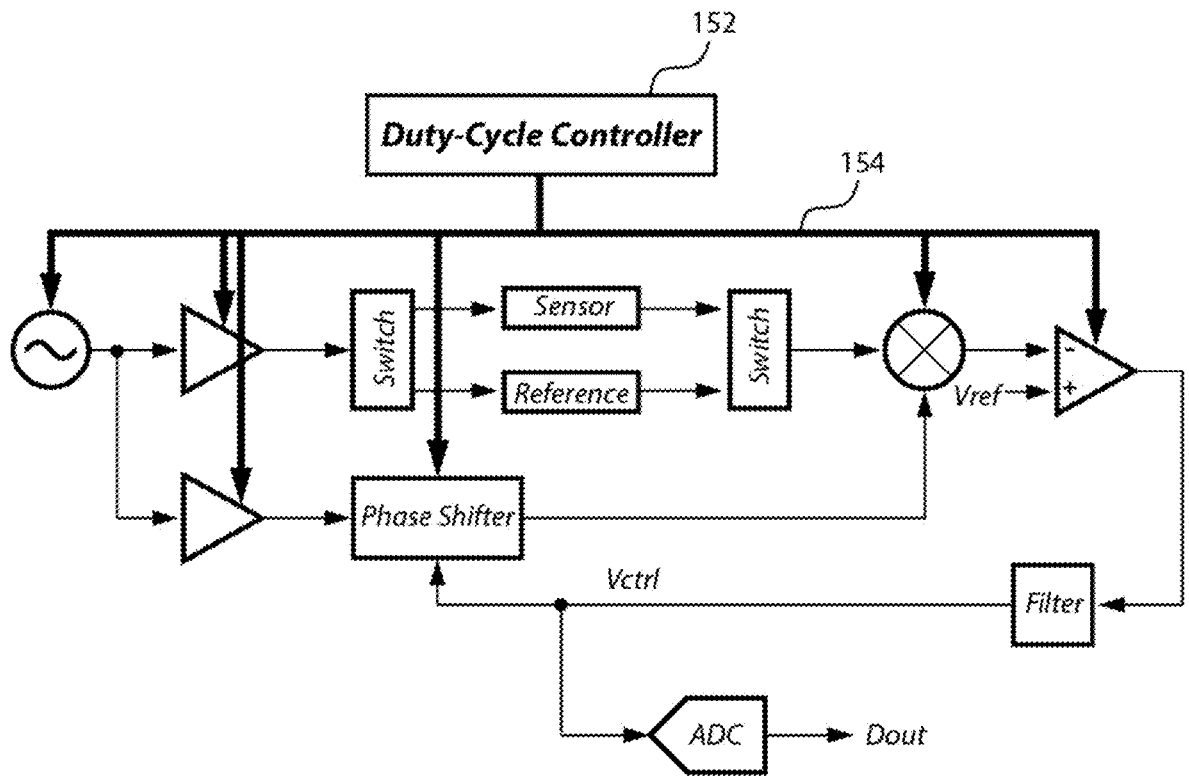
FIG. 2G is a system block diagram with duty-cycle controller.

The RF pulses used to excite the transmission lines can be turned on and off by various methods. In some embodiments, a duty-cycle controller 152 can be incorporated into the system (FIG. 2G) which generates a power-gating signal 154 to generate the pulses or bursts. These pulses/bursts will often be at a sampling rate of about 10 to 400 samples per second. Duty cycling methods are not the only way to produce narrow pulses, but duty cycling can help reduce power, since the electronics controlled by the duty-cycle can be sleeping (drawing essentially no power) during the off phase of the duty-cycle.

Figure 2H:
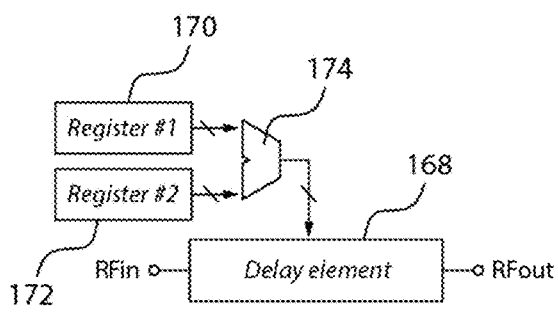
FIG. 2H is a flow graph for systematic offset calibration.

In some embodiments, the systematic offset is nulled prior to the heart-rate measurements. This is achieved by calibrating the phase shift of the RF carrier signal in the sensing and the reference modes. FIG. 2H exhibits the calibration flow graph. First, the RF carrier signal is directed toward the reference transmission line. The delay (or the phase shift) of a tunable delay element 168 is digitally controlled such that the integrator output is nulled. The delay (or the phase shift) setting is then stored in the registers 170. Next, the RF carrier signal is directed toward the sensing transmission line. The delay (or the phase shift) of the delay element can be digitally controlled such that the integrator output is nulled. The delay (or the phase shift) setting is then stored in another registers 172. During the measurement of the heart-rate signal, the delay (or the phase shift) setting is alternated between the two registered through a set of multiplexers 174 in accordance with the chopping modes to keep the sensor output at the optimum sensitivity mode.

Thus, as shown in FIG. 2H, the steps are:

Direct RF signals to the reference element; null the integrator output by digitally controlling the delay (or the phase shift) of the delay element and store the control signal in register 1.

Direct the RF signal to the sensing element; null the integrator output by digitally controlling the delay (or the phase shift of the delay element), and store the control signal in register 2.

Enable the chopping operation to measure heart rate—alternate between the control signal stored in register 1 and register 2 through a clocked multiplexer.

Figure 2I:
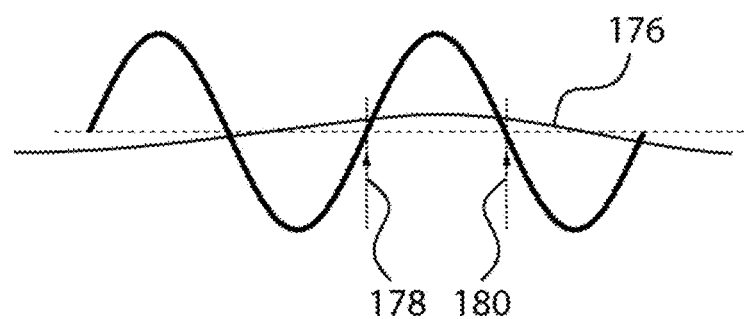
FIG. 2I is an illustration of the impact of the flicker noise on the RF signal.
Figure 2J:
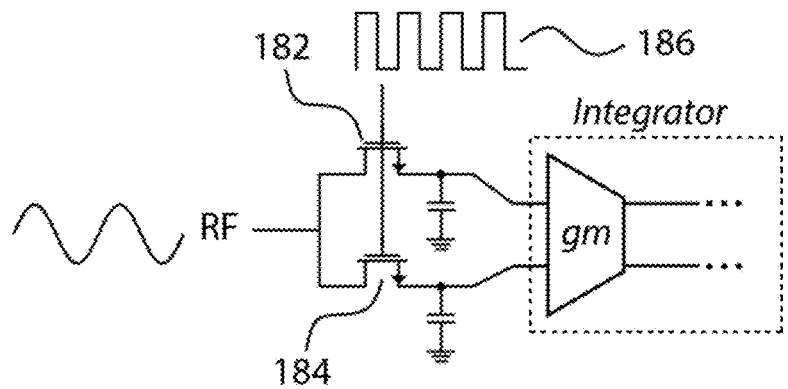
FIG. 2J is a schematic for double-edges correlated-double sampling scheme using second harmonic sampling.
Figure 2K:
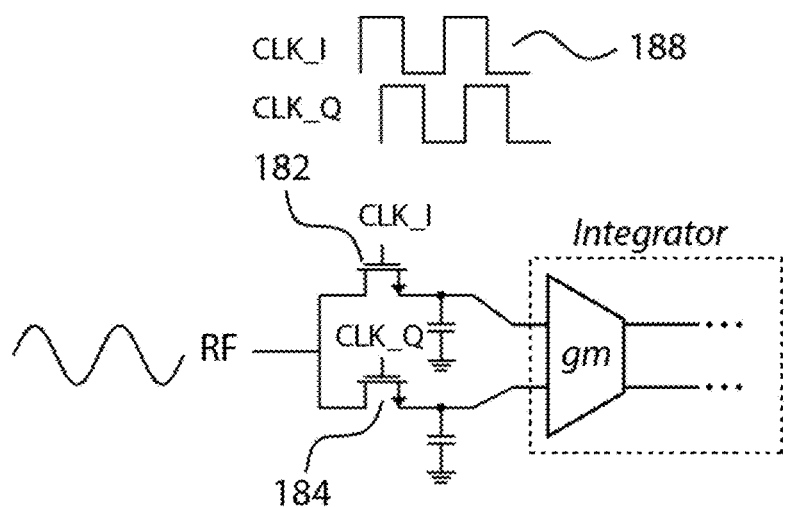
FIG. 2K is a schematic for double-edges correlated-double sampling scheme using quadrature clocks sampling.

In some embodiments, the flicker noise that is common in both the chopping modes, such as those generated by the driving inverters and the integrators, can be alleviated by the chopping modulation. However, the flicker noise generated by the RF switches 160 are inevitably modulated to the chopping frequency and cannot be distinguished from the actual heart-rate signal since the noise presented by these switches are uncorrelated with respect to each other. In one embodiment, a double-edge correlated-double sampling (CDS) technique is can be used to remedy such modulation mechanism. FIG. 2I shows the signal waveform with the switch flicker noise modeled as an additive offset 176. By taking the difference between the signals sampled at both the rising edges 178 and the falling edges 180 of the RF carrier signal, such a common drift is effectively cancelled. The sampling clocks for both the rising-edge sampler 182 and the falling-edge sampler 184 can be generated at twice the RF frequency 186 (FIG. 2J) or by using a pair of quadrature clocks 188 (FIG. 2K).

As previously discussed, in a preferred, embodiment, all of the narrow-band Gigahertz frequency signal pulses/bursts that the invention emits over a plurality of time intervals (during the course of a physiological measurement such as determining a heartbeat pulse rate) are emitted at the same frequency. It is important to avoid frequency drift both within and between such pulses/bursts, because such drift can throw off the measurements, resulting in error.

In some embodiments, the invention insures that the signal pulses/bursts are all emitted at the same frequency by using various techniques. For example, the same frequency may be maintained or stabilized by using various temperature compensation and phase-locked loop methods, such as the methods described below.

In some embodiments, the excitation source 12 can be implemented with an open-loop voltage-controlled oscillator (VCO) in SiGe, CMOS, or other semiconductor technologies. As the split signals 46 and 48 are self-mixed at the mixer 18, the phase noise arising from the source 12 is canceled. Such an interferometry-based architecture improves the signal-to-noise ratio (SNR) and saves a considerable amount of power. To improve the frequency stability, the excitation source can be temperature compensated using an on-chip temperature sensor. The excitation frequency can range from 0.5 to 60 GHz and can be selected according to the sensor design. In the low GHz regime, a temperature-compensated MEMS-based oscillator featuring high-Q MEMS resonator can be utilized for further power saving. At the high-frequency regime, it may be preferable to use a SiGe or CMOS oscillator, and the frequency stability can be improved by using phase-locked loop (PLL) methods.

In some embodiments, the driving amplifiers 14 and 16 may be implemented using nonlinear amplifiers such as class-B/C/D/E/F amplifiers for optimum power efficiency as compared to the conventional class-A amplifiers. Passive harmonic filters following the amplifiers can be included to reject high-order harmonics.

As previously discussed, in order to provide a good "control" or "reference" signal that mimics many aspects of the sensor signal 6, but lacks physiological modulation, it will often be useful to configure the one or more reference transmission line(s) 8 to shield or block any near field energy from the user. This can include near field energy from the sensing transmission line 6 that may have penetrated at least partially into the user's blood vessels (e.g. penetrated into or past the user's skin).

In some embodiments, the near-field sensors may be implemented using planar multi-layer printed circuit boards (PCBs). FIG. 3A shows the schematic of a sensing/reference pair where two stripline-based transmission lines are implemented side-by-side with transmission line 62 serving as a reference sensor and transmission line 64 serving as the heart-rate detector. Shared top and bottom metal layers 66 serve as the ground planes for the return currents of both the reference 62 and the sensing transmission lines 64.

In addition to helping to set near field gap distances, these ground planes can also offer shielding to the signal lines and minimizes any external interference. In one embodiment, the ground planes may be coated with a protecting layer 68 to prevent any corrosion of the metals. The protecting layer can comprise non-conductive materials, e.g. plastic, polyimide, or rubber, where fields can easily penetrate through. This property allows the invention to be integrated inside the existing wearable or consumer platforms without changing their appearance, and thus become "invisible". Vias connecting the top and the bottom ground planes may be distributed along the signal lines, minimizing the unwanted higher-order propagating modes while isolating the sense 64 and the reference 62 transmission lines.

An aperture or gap 70 is often opened on the top ground plane above the sensing line 64 to allow the electromagnetic fields to fringe out of the device from the sensing section 72 (part of the sensing line 64 that is exposed by the gap or aperture) for blood volume detection. This aperture helps determine how far the fringing fields may extend from the device.

The size of this aperture or gap may vary. In some embodiments, the at least one transmission line configured to emit near field fringing energy can comprise a width of between 0.1 millimeters to 3 millimeters. The aperture or gap here may comprise a gap between 0.2 and 10 millimeters between the transmission line and a nearby ground plane.

Thus this aperture or gap is traversed by the near-field fringing energy when the transmission line is excited by the Gigahertz frequency signal. Assuming that the aperture or gap is configured to be disposed proximate the skin, then at many excitation frequencies, the depth of the fringing near field will be on the same dimensions as the gap, and will penetrate into the user's skin according to the approximate dimensions of the gap. By adjusting excitation frequencies and aperture dimensions, the distance that the near field extends away from the transmission line can be relatively precisely controlled as desired, often so that the near field penetrates to dimensions of between 0.2 to 10 millimeters below the skin, and with an area also defined by the gap or aperture.

Figure 3A:
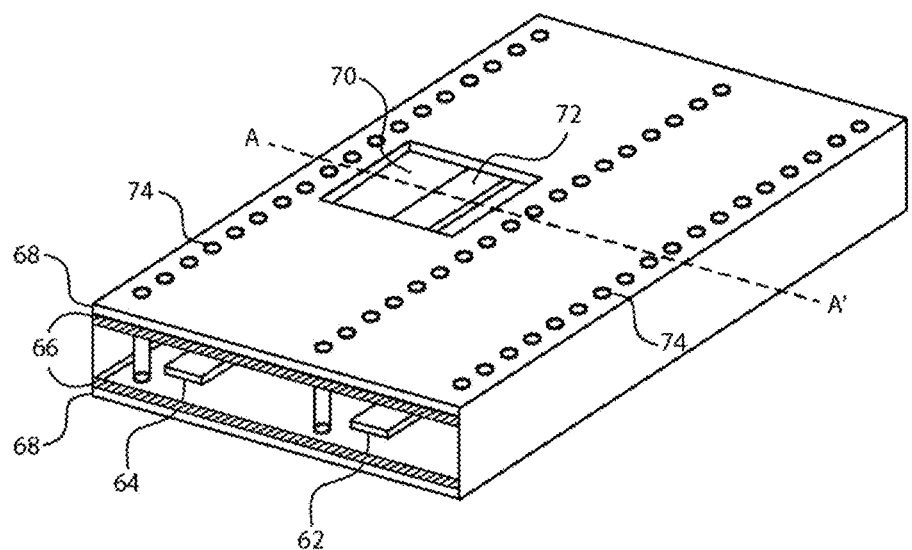
FIG. 3A is a schematic of the planar electromagnetics sensors in a stripline configuration.
Figure 3B:
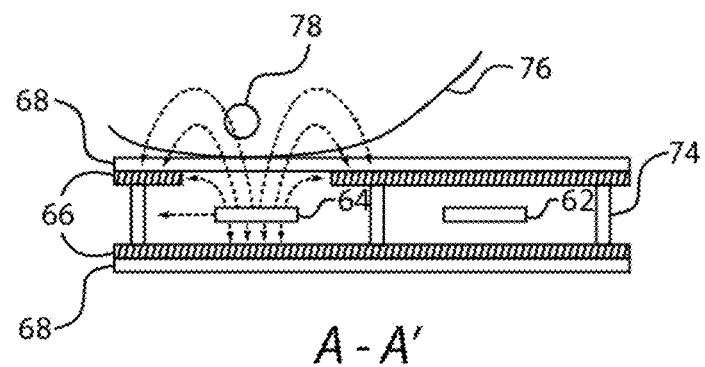
FIG. 3B is a cross-section view of the planar electromagnetics sensors in a stripline configuration.
Figure 3C:
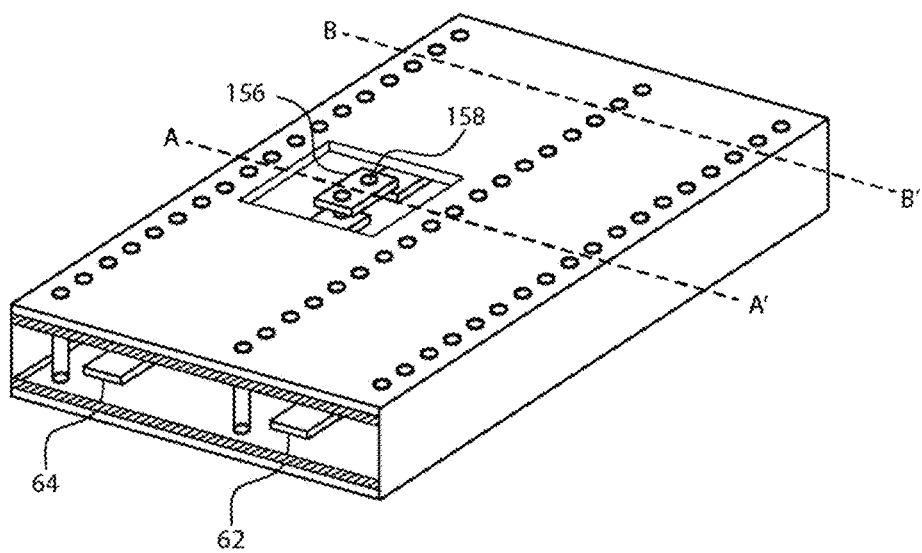
FIG. 3C is a schematic of the planar electromagnetics sensors in a stripline configuration with elevated sensing electrode.
Figure 3D:
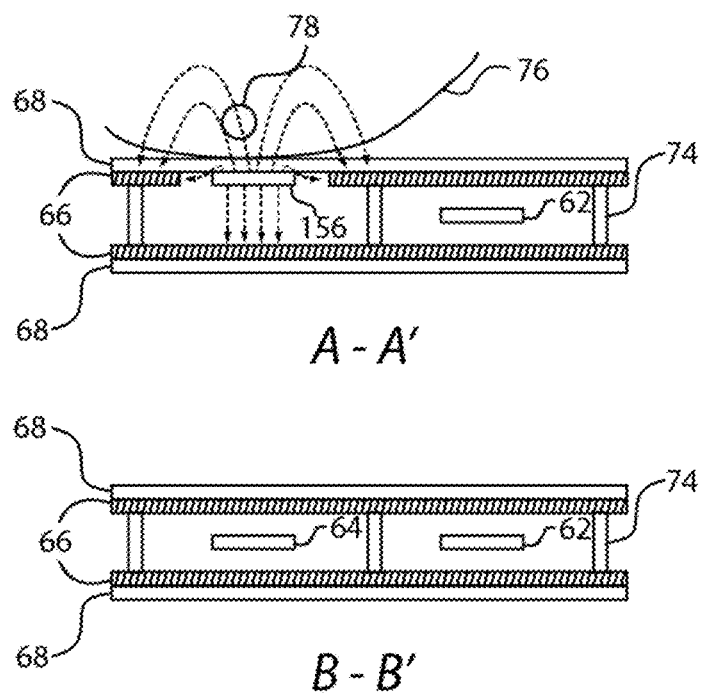
FIG. 3D is a cross-section view of the planar electromagnetics sensors in a stripline configuration with elevated sensing electrode.

These sensing fields, after penetrating through the skin 76 and the user blood vessels 78, are terminated at the top ground planes 66, as shown in FIG. 3B. As the transmission lines are broadband in nature, in some embodiments a multi-frequency excitation can be employed to increase the dimensions of the detected signal. In some embodiments, the sensing transmission line may be transitioned or placed on or near the upper metal layer in order to enhance the sensitivity. FIG. 3C shows such an arrangement where via 158 is used to provide a layer transition to the actual sensing segment 156. FIG. 3D shows the cross section of FIG. 3C.

Figure 3E:
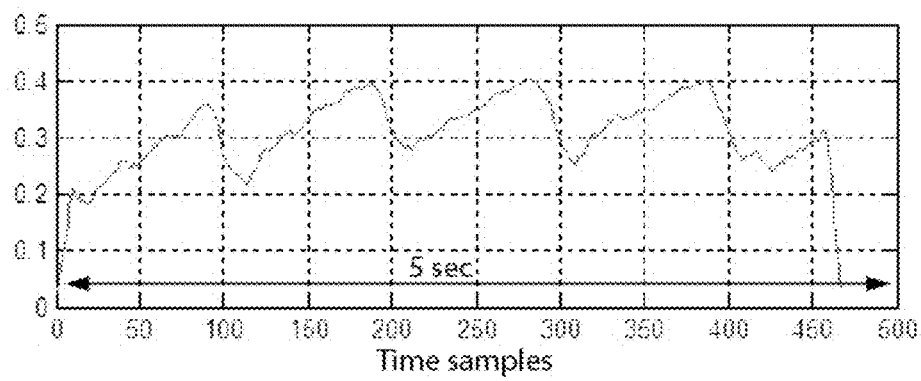
FIG. 3E is a measured heart-rate waveform from the planar electromagnetics sensors in a stripline configuration with elevated sensing electrode.

FIG. 3E shows an experimentally determined measured heart-rate waveform obtained from a user's index finger that was placed on the invention's aperture or gap from FIG. 3C, with the signals processed according to the methods previously described in FIG. 2C to 2H.

In some embodiments, the user's heart rate may be determined by using the system's processor to find (extract) the peaks and the valleys from the measured signal. This can be accomplished by, for example, applying a sliding window of 100-msec timing interval across the measured raw signal. The timing indices of either the local maximum or the local minimum can be recorded and the heart rate can be calculated by inverting the timing distance between the successive peaks or valleys. Here the heart rate can be expressed in forms of frequency, where the units are beats per minute (BPM).

According to the invention, various types of transmission line configurations may be used. As previously discussed, the transmission line may be configured using at least one planar stripline-based transmission line mounted on at least one planar multilayer printed circuit board.

As discussed below, the transmission line may also be configured using at least one grounded coplanar waveguide, or according to at least one ring-shape resonator loaded transmission line.

Figure 4A:
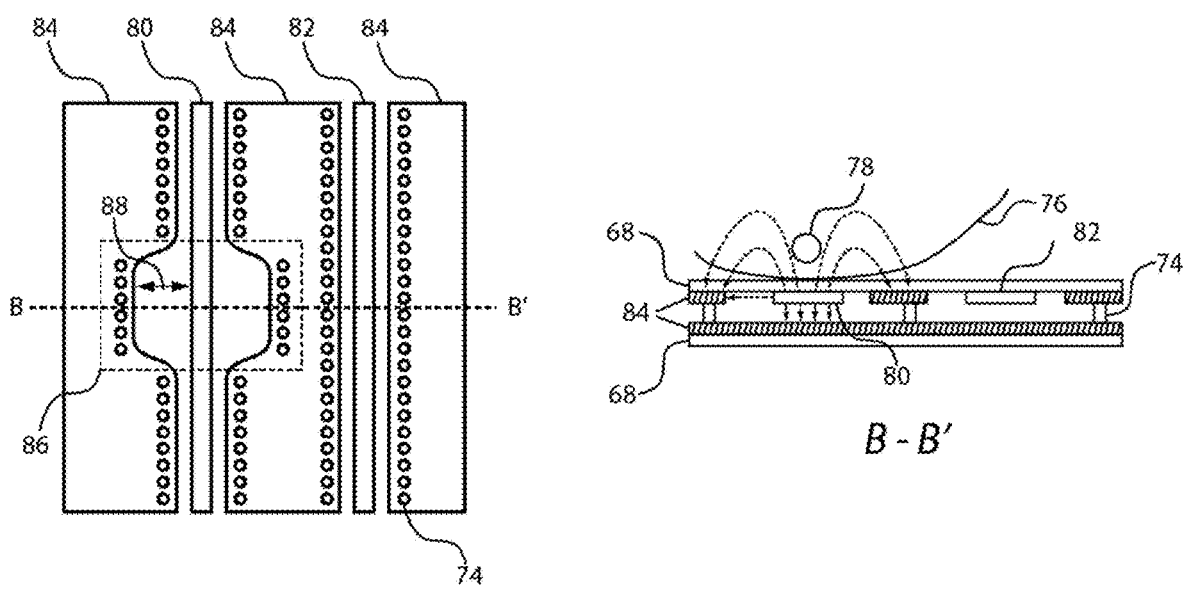
FIG. 4A is a schematic of the planar electromagnetics sensors in grounded coplanar waveguide configuration.

FIG. 3A, FIG. 3C, and FIG. 4A are three examples of such a transmission line. They are different in geometry and different in layers.

Thus the invention's electromagnetic sensor can be implemented using various types of transmission lines. FIG. 4A shows the schematic of a pair of grounded coplanar waveguide (GCPW) in which transmission line 80 performs sensing, while transmission line 82 serves as the reference. Ground planes 84 provide the return path for the RF currents and are connected through a bottom layer ground plane using arrays of vias 74. In such a topology, the fringing distance of the sensing fields in the sensing aperture 86 is dependent on the gap 88 between the signal lines 80 and the ground planes 84 and can be adjusted to maximize the level of the heart-rate signals.

Figure 4B:
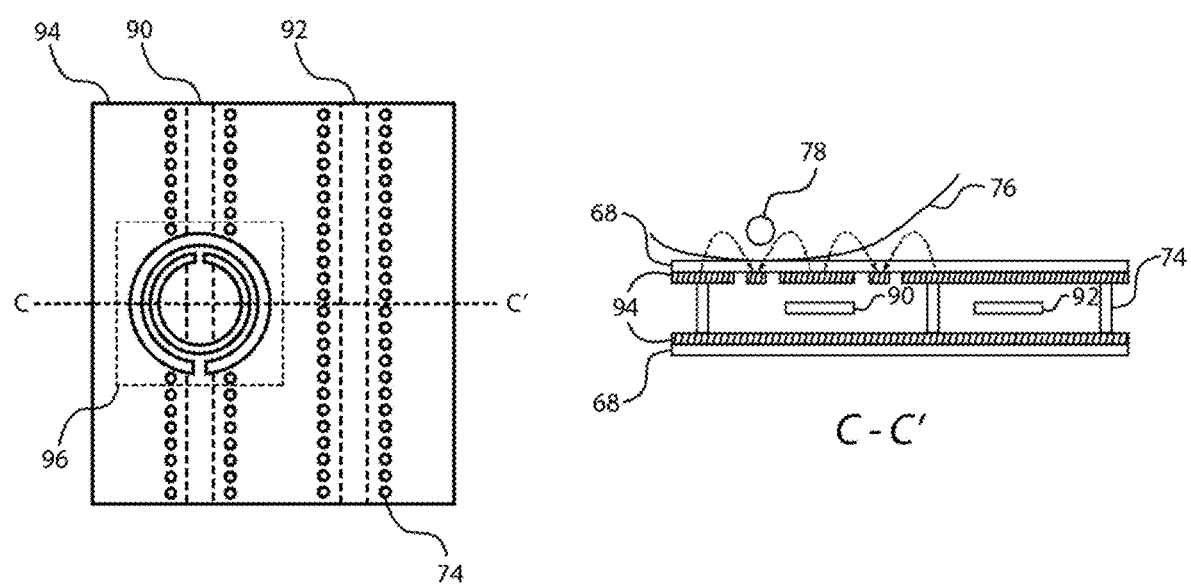
FIG. 4B is a schematic of the planar electromagnetics sensors in complementary split-ring-resonator configuration.
Figure 4C:
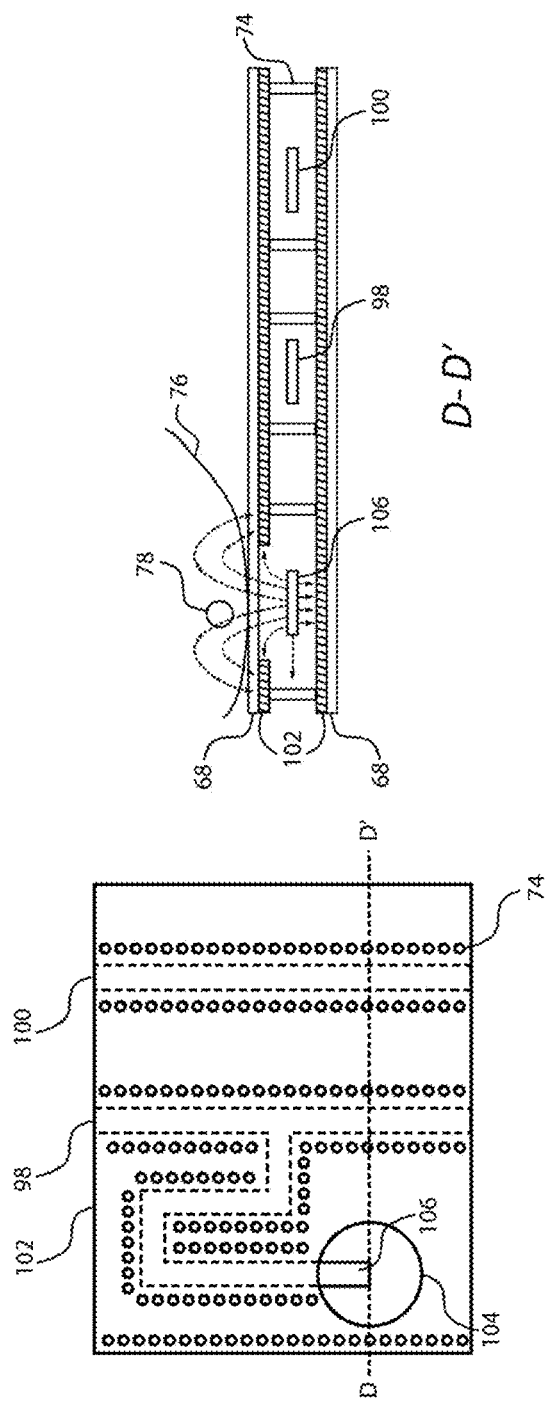
FIG. 4C is a schematic of the planar electromagnetics sensors in stub-loaded transmission-line configuration.

FIG. 4B and FIG. 4C show the schematics of another type of planar sensors. In FIG. 4B, a ring-shape resonator, termed complementary split-ring-resonator (CSRR), is depicted. The CSRR 96 consists of an inner and an outer ring, which are implemented by etching and removing the metal in the top ground plane 94. Each ring has a short piece of metal at one end of the ring. The sensing transmission line 90 is used to excite the resonance of the ring whereas transmission line 92 serves as the reference. By exciting the ring close to its resonance frequencies, the fringing fields between the gaps are maximized. With the presence of the artery, the fields are altered by the changes in the blood volume, which in turns perturbs the resonance frequency. Therefore, the CSRR sensor offers signal enhancement through measuring the changes of the sharp peaks (or notches) created around the resonance frequencies.

In FIG. 4C, a stub-loaded transmission line 98 is used as the sensor. The stub 106 acts similarly as a resonator and hence its resonance frequency is sensitive to the loading on the open-ended aperture 104. The stripline 100 is used as the reference and the ground plane 102 implemented in the top metal layer is used for shielding. To benefit from signal enhancement in the resonator-based approach, the excitation source needs to be adjusted to match the resonance frequencies of the resonator using a frequency calibration loop prior to the heart-rate detection.

Put alternatively, FIG. 4B and FIG. 4C show some alternative approaches. FIG. 4B shows a split-ring-resonator and FIG. 4C shows a quarter-wavelength resonator with an open end for fields to fringe.

These resonators may be inserted at an arbitrary point on the main transmission line. These act to divert the energy of the guided waves from the main transmission line and absorb that energy into the resonator. As the arteries are presented to the resonators, for example during a finger touch, the motion of blood through the blood vessels acts to interact and to change how these resonators absorb the wave's energy. By measuring these energy changes, the invention can again gain more information pertaining to the cardiovascular status of the user. Here both the energy of the waves, and the phase of the waves, will both vary according to the cardiovascular status (e.g. heart rate) of the user, and either the amplitude or phase of the received waves can be used to infer heart rate.

Figure 5A:
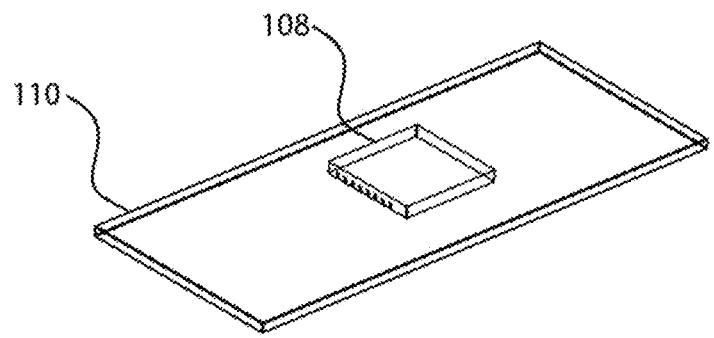
FIG. 5A is a front-side illustration of system integration using a rigid printed circuit boards.
Figure 5B:
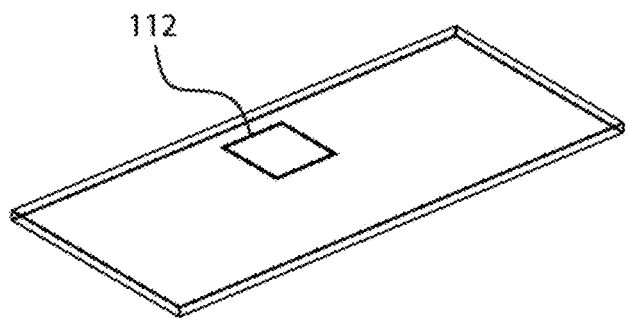
FIG. 5B is a back-side illustration of system integration using a rigid printed circuit boards.

FIG. 5A-FIG. 5D show how the electronics and the planar sensors can be integrated, according to the invention. In FIG. 5A and FIG. 5B, the planar sensors can be implemented using rigid PCB 110. FIG. 5A shows the front side of this configuration, and FIG. 5B shows the back side of this configuration.

As shown in FIG. 5A, the electronics 108 can be mounted on top of the PCB. As shown in FIG. 5B, on the backside, an aperture 112 is used to allow the fields to fringe from the sensor into the skin for blood volume detection in the artery.

Figure 5C:
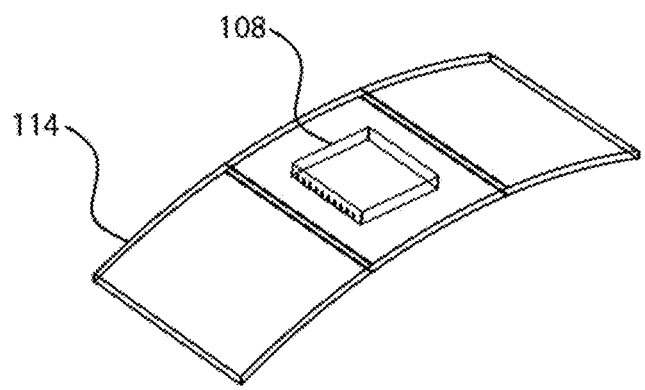
FIG. 5C is a front-side illustration of system integration using a flexible printed circuit boards.
Figure 5D:
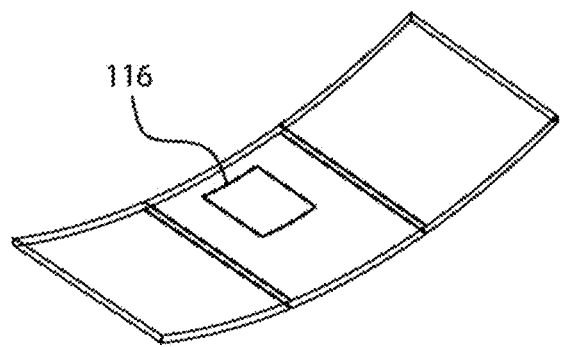
FIG. 5D is a back-side illustration of system integration using a flexible printed circuit boards.

In FIG. 5C and FIG. 5D, the planar sensors are implemented using flexible PCB 114. FIG. 5C shows the front side, and FIG. 5D show the back side of this configuration. As shown in FIG. 5C, the electronics 108 are mounted on top of the flexible PCB. As shown in FIG. 5D, on the backside, an aperture 116 is used to allow the fields to fringe from the sensor into the skin for blood volume detection in the artery. In both cases, a protecting layer can cover the aperture, which can comprise a non-conductive material where fields can easily penetrate through. This property allows the invention to be integrated inside the existing wearable or consumer platforms without changing their appearance, and thus become effectively "invisible".

It should be evident that because the invention can be implemented in a relatively small area, requiring low power, it may be incorporated as a component of other devices. For example, the invention's at least one transmission line (and other components as desired) may be disposed in various user worn configurations, as well as mounted on various types of external devices that the user may touch.

Figure 6A:
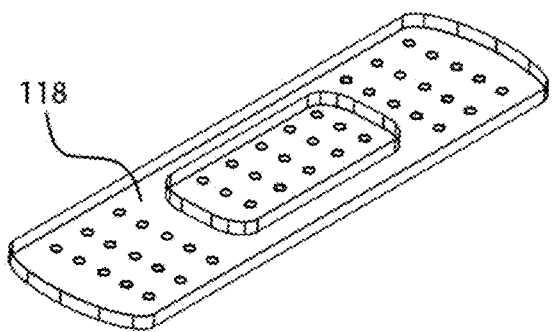
FIG. 6A is a front-side illustration of the invention embedded in a patch/bandage.
Figure 6B:
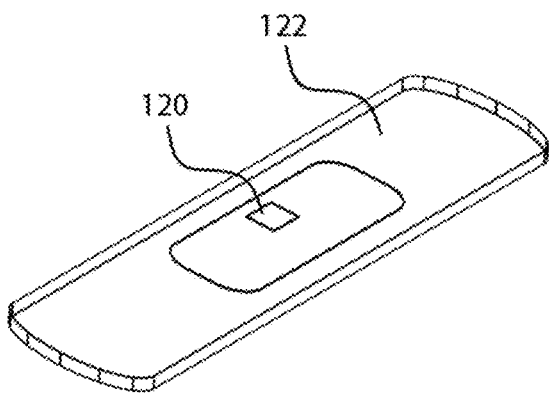
FIG. 6B is a back-side illustration of the invention embedded in a patch/bandage.
Figure 7A:
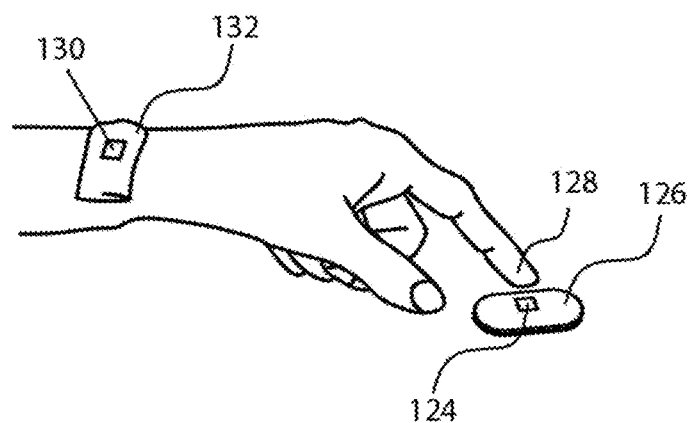
FIG. 7A is an illustration depicting the usability of the invention as a touch sensor.
Figure 7B:
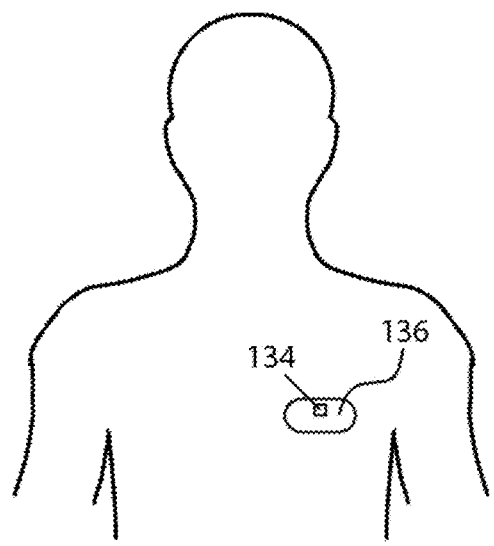
FIG. 7B is an illustration depicting the usability of the invention as a chest patch.
Figure 7C:
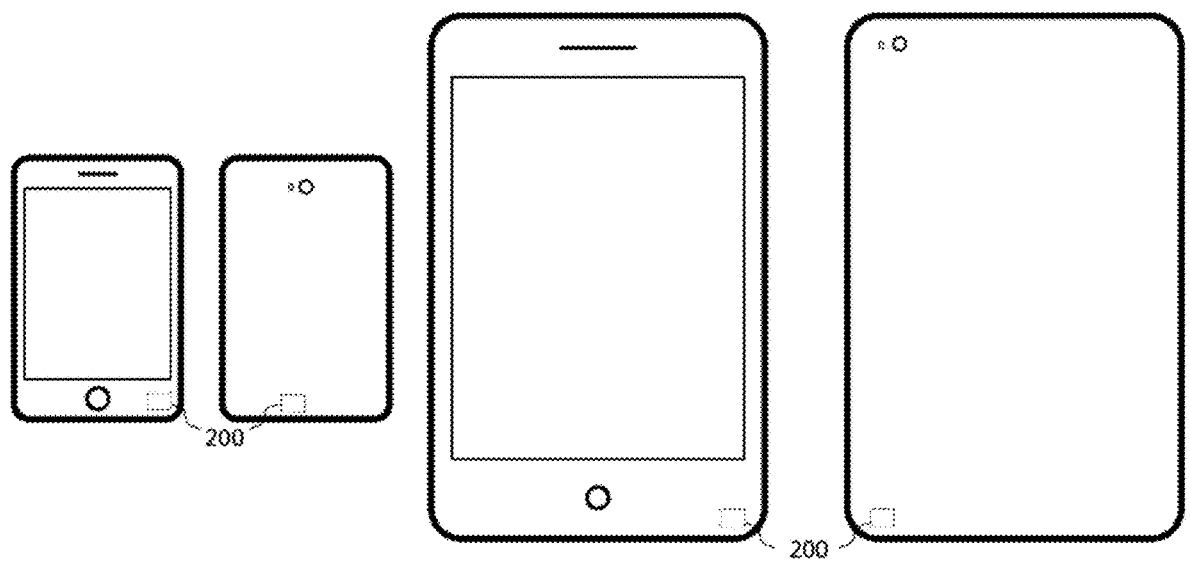
FIG. 7C is an illustration depicting the usability of the invention as a touch device embedded in a smart phone or a tablet.
Figure 7D:
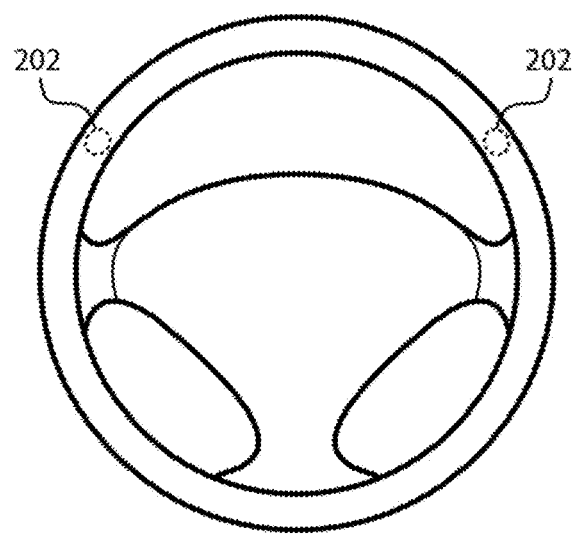
FIG. 7D is an illustration depicting the usability of the invention as a touch device embedded in a driving wheel.

FIG. 6A and FIG. 6B shows the integration of the heart-rate sensing device in a patch/bandage 118. FIG. 6A shows the front of this configuration, while FIG. 6B shows the backside of this configuration. As FIG. 6B shows, on the backside of the patch/bandage, the sensing aperture 120 is surrounded by an adhesive 122 to enable direct attachment of the patch/bandage onto the human skin for long-term monitoring. In some embodiments, a flexible PCB, such as that previously shown in FIG. 5C may be utilized to be amenable to the skin curvature.

FIG. 7A-FIG. 7D shows some examples of usage of the invention on the human body. The heart-rate monitoring device 124 can be implemented as a touch device 126 integrated in the front or the backside of a cell phone or a tablet 200 where the heart rate is detected by the blood vessels at the fingertips 128. In addition, the heart-rate monitoring device 130 can be embedded in a wristband or a watch 132 where the heart rate is detected by blood vessels in the wrist. Moreover, the heart-rate monitoring device 134 can be mounted on the chest 136, similar to an ECG sensor. Finally, the sensor can be integrated into a driving wheel 202 which monitors the drivers' physiological condition to improve driving safety.

Comparative Power Analysis:

Compared to prior art methods, such as photometric methods employing pulsed light emitting diodes and photodetectors, the methods described herein can operate with up to two orders of magnitude lower power use.

Consider a prior-art method that operates by pulsing (or duty cycling) an LED to determine a heart-rate measurement. Such LEDs often require comparatively higher voltages and currents, such as use of 3.3 Volts and 100 mA LED. The LEDs are not excited continuously; instead the LEDs are duty-cycled with pulses having a pulse-width at tens of microseconds, e.g. 30 microseconds. The prior art system would use about 1 milliwatts at a sampling rate of 100 samples per second.

By contrast, according to the invention, in the prototype discussed in FIG. 3E, the electronics itself uses about 30 milliwatts while running continuously and the improved properties of the near field measurements allow adequate measurements to be made in only 3 microseconds. Assuming the same low sample rate of 100 Hz, the invention would use about 100 times less energy per second to operate.

Sensor Fusion Methods:

In some embodiments, it may be useful to combine the fringing near-field sensors of the present invention with other cardiovascular status sensors in order to produce a more comprehensive view of patient cardiovascular status. As one example, the fringing near-field sensor may be combined with an optically based blood oximeter. The blood oximeter may be mounted on the same device holding the fringing near-field sensor, or on an alternative device. In this manner, cardiovascular status data obtained from the fringing near-field sensor, such as heartbeat, may be compared to changes in blood oxygen levels during the same heartbeat, and additional insights into the physiology of the user may therefore be obtained.

In some embodiments, the invention can be distributed at different locations on a human body to collect different cardiovascular information. By coupling with different sensing devices, such as multi-wavelength optical pulse oximetry and a temperature sensor, the system enables sensor fusion and the extraction of other physiological information such as glucose level and blood pressure using machine-learning algorithm.

The invention claimed is:

1. A method of using near-field fringing energy to obtain user cardiovascular information, said method comprising:
providing at least one transmission line configured to guide electromagnetic waves and to emit near-field fringing energy through at least one transmission line gap, and disposing said at least one transmission line gap proximate a skin of a user so that said near-field fringing energy emitted by said at least one transmission line gap, when operating at Gigahertz frequencies, extends up to a corresponding wavelength $\lambda$ of said Gigahertz frequency away from said transmission line as to penetrate at least partially into blood vessels of said skin;
wherein said Gigahertz frequency is between 0.5 to 60 GHz, and wherein said wavelength $\lambda$ is between c/0.5 GHz and c/60 GHz, where c is the speed of light;
exciting said at least one transmission line with narrow-band Gigahertz frequency signal pulses over a plurality of time intervals, and obtaining data by measuring changes in any of a phase or amplitude of said near-field fringing energy over said plurality of time intervals;
and using at least one processor, and said data, to determine at least the heart rate of said user.

2. The method of claim 1, wherein said Gigahertz frequency further comprises a narrow-band Gigahertz frequency
with a bandwidth of less than 0.01 GHz (10 MHz) and said pulses comprise pulses with a time duration of less than 5 microseconds.

3. The method of claim 1, wherein said at least one transmission line comprises at least one sensing transmission line and at least one reference transmission line, further exciting said at least one sensing transmission line and said at least one reference transmission line using any of time-division multiplexing and chopping stabilization so as to alternate said narrow-band Gigahertz frequency signal pulses between said at least one sensing transmission line, and said at least one reference transmission line;

measuring changes in any of said phase or amplitude of said near-field fringing energy from said at least one sensing transmission line and said at least one reference transmission line over said plurality of time intervals;

and using changes in any of said phase or amplitude of said near-field fringing energy obtained from said at least one reference transmission line to correct said data for noise or drift.

4. The method of claim 3, wherein said at least one reference transmission line is configured to shield or block any near field energy from said sensing transmission line that penetrates at least partially into said blood vessels of said skin.

5. The method of claim 3, further using changes in any of said phase or amplitude of said near-field fringing energy obtained from said at least one reference transmission line, and automatic feedback adjustment to correct for any of:
   a) skin-sensor contact variations;
   b) changes caused by noise or drift in any of said phase or amplitude of said near-field energy obtained from said at least one sensing transmission line.

6. The method of claim 3, wherein changes in the phase of said near-field fringing energy from at least said at least one sensing transmission lines are obtained by any of
   a) detecting physiologically modulated RF carrier signals from said at least one transmission lines, and using a mixer and a phase adjustable local oscillator (LO) to detect physiologically induced changes in the phase of said physiologically modulated RF carrier signals;
   b) adjusting the phase of an RF signal that excites said at least one sensing transmission line and said at least one reference transmission line, and using any of multiplexing or chopping methods to switch back and forth between said at least one sensing transmission lines and said at least one reference transmission lines, and comparing phase changes between said detected physiologically modulated RF carrier signals from said at least one sensing transmission line, and detected non-physiologically modulated RF carrier signals form said at least one reference transmission line; and
   c) further removing noise by using double-edges correlated-double sampling methods.

7. The method of claim 1, wherein said at least one transmission line is configured using any of:
   a) at least one planar stripline-based transmission line mounted on at least one planar multilayer printed circuit board;
   b) at least one grounded coplanar waveguide;
   c) at least one ring-shape resonator loaded transmission line.

8. The method of claim 1, wherein said at least one transmission line configured to emit near field fringing energy further comprises a width of between 0.1 millimeters to 3 millimeters, and a gap of between 0.2 and 10 millimeters between said transmission line and a nearby ground plane;
   wherein said gap is traversed by said near-field fringing energy when said at least one transmission line is excited by said Gigahertz frequency signal pulses; and
   said gap is configured to be disposed proximate said skin.

9. The method of claim 1, wherein all of said narrow-band Gigahertz frequency signal pulses over a plurality of time intervals are emitted at a same frequency, and wherein said same frequency is stabilized by any of temperature compensation of phase-locked loop methods.

10. The method of claim 1, wherein all of said narrow-band Gigahertz frequency signal pulses over a plurality of time intervals are emitted at a plurality of discrete, narrow bandwidth, frequencies.

11. The method of claim 1, wherein, at least at distances than $\lambda$, said at least one transmission line also functions as an antenna and emits far-field Gigahertz frequency electromagnetic radiation, and wherein said near-field is any of:
   1: a reactive near-field, wherein said near-field fringing energy emitted by said at least one transmission line, when excited at Gigahertz frequencies extends up to $\lambda/2\pi$ times a wavelength of said Gigahertz frequency away from said at least one transmission line; or
   2: a Fresnel near-field, wherein said near-field fringing energy emitted by said at least one transmission line extends up to the wavelength $\lambda$; or
   3: said near-field fringing energy penetrates on an order of a width of a gap between said at least one transmission line and a nearby ground plane.

12. The method of claim 1, wherein said at least one transmission line is disposed in either a user worn configuration, or is mounted on an external device that said user touches.

13. A device for obtaining user cardiovascular information by near-field fringing energy, said device comprising:
   at least one transmission line configured with a transmission line gap to emit near-field fringing energy when disposed proximate a skin of a user so that said near-field fringing energy emitted by said at least one transmission line gap, when operating at Gigahertz frequencies, extends up to a corresponding wavelength $\lambda$ of said Gigahertz frequency away from said transmission line as to penetrate at least partially into blood vessels of said skin;
   wherein said Gigahertz frequency is between 0.5 to 60 GHz, and wherein said wavelength $\lambda$ is between c/0.5 GHz and c/60 GHz, where c is the speed of light;
   a transmitter device configured to excite said at least one transmission line with narrow-band Gigahertz frequency signal pulses over a plurality of time intervals;
   a receiver device and at least one processor configured to obtain data by measuring changes in any of a phase or amplitude of said near-field fringing energy over said plurality of time intervals, and to use said data to determine at least the heart rate of said user.

14. The device of claim 13, wherein said transmitter device is further configured to emit said Gigahertz frequency as narrow-band Gigahertz frequency with a bandwidth of less than 0.01 GHz (10 MHz); and
   said pulses comprise pulses with a time duration of less than 5 microseconds.

15. The device of claim 13, wherein said at least one transmission line comprises at least one sensing transmission line and at least one reference transmission line;
   wherein said transmitter device and said processor are configured to excite said at least one sensing transmission line and said at least one reference transmission line using any of time-division multiplexing and chopping stabilization so as to alternate said narrow-band Gigahertz frequency signal pulses between said at least one sensing transmission line, and said at least one reference transmission line;
   wherein said receiver device and said processor are configured to obtain data by measuring changes in any of said phase or amplitude of said near-field fringing energy from said at least one sensing transmission line and said at least one reference transmission line over said plurality of time intervals; and wherein said device is further configured to use changes in any of said phase or amplitude of said near-field fringing energy obtained from said at least one reference transmission line to correct said data for noise or drift.

16. The device of claim 15, wherein said at least one reference transmission line is configured to shield or block any near field energy from said sensing transmission line that penetrates at least partially into said blood vessels of said skin.

17. The device of claim 15, wherein said device is configured to use changes in any of said phase or amplitude of said near-field fringing energy obtained from said at least one reference transmission line, and automatic feedback adjustment to correct for any of:
  a) skin-sensor contact variations;
  b) changes caused by noise or drift in any of said phase or amplitude of said near-field energy obtained from said at least one sensing transmission line.

18. The device of claim 13, wherein said at least one transmission line is configured using any of:
  a) at least one planar stripline-based transmission line mounted on at least one planar multilayer printed circuit board;
  b) at least one grounded coplanar waveguide;
  c) at least one ring-shape resonator loaded transmission line.

19. The device of claim 13, wherein said at least one transmission line configured to emit near field fringing energy further comprises a width of between 0.1 millimeters to 3 millimeters, and a gap of between 0.2 and 10 millimeters between said transmission line and a nearby ground plane;
  wherein said gap is traversed by said near-field fringing energy when said at least one transmission line is excited by said Gigahertz frequency signal pulses; and
  said gap is configured to be disposed proximate said skin.

20. The device of claim 13, wherein said device transmitter is configured by any of temperature compensation or phase-locked loop methods to emit all of said narrow-band Gigahertz frequency signal pulses over a said plurality of time intervals at a same frequency.

21. A method of obtaining user cardiovascular information, said method comprising:

providing at least one transmission line configured to guide electromagnetic waves and to emit near-field fringing energy, and disposing said at least one transmission line proximate a skin of a user so that said near-field fringing energy emitted by said at least one transmission line, when operating at Gigahertz frequencies, extends away from said transmission line as to penetrate at least partially into blood vessels of said skin;

exciting said at least one transmission line with narrow-band Gigahertz frequency signal pulses over a plurality of time intervals, and obtaining data by measuring changes in any of a phase or amplitude of said near-field fringing energy over said plurality of time intervals;

and using at least one processor, and said data, to determine at least the heart rate of said user;

wherein said at least one transmission line comprises at least one sensing transmission line and at least one reference transmission line, further exciting said at least one sensing transmission line and said at least one reference transmission line using any of time-division multiplexing and chopping stabilization so as to alternate said narrow-band Gigahertz frequency signal pulses between said at least one sensing transmission line, and said at least one reference transmission line;

measuring changes in any of said phase or amplitude of said near-field fringing energy from said at least one sensing transmission line and said at least one reference transmission line over said plurality of time intervals;

and using changes in any of said phase or amplitude of said near-field fringing energy obtained from said at least one reference transmission line to correct said data for noise or drift.

\* \* \* \* \*